United States Patent [19]

Galli

[11] Patent Number: 5,681,291

[45] Date of Patent: Oct. 28, 1997

[54] DISPOSABLE AUTO-INJECTOR FOR PREFILLED SYRINGES

[75] Inventor: Rosaria Galli, Camogli, Italy

[73] Assignee: Tebro S.A., Luxembourg, Luxembourg

[21] Appl. No.: 446,614

[22] PCT Filed: Oct. 18, 1993

[86] PCT No.: PCT/EP93/02863

§ 371 Date: Jul. 20, 1995

§ 102(e) Date: Jul. 20, 1995

[87] PCT Pub. No.: WO94/11041

PCT Pub. Date: May 26, 1994

[30] Foreign Application Priority Data

Nov. 19, 1992 [IT] Italy ................... GE92A0120
Jul. 28, 1993 [IT] Italy ................... GE93A0069

[51] Int. Cl.⁶ ........................ A61M 5/32; A61M 5/20
[52] U.S. Cl. .................... 604/192; 604/156; 604/162; 604/198
[58] Field of Search .................... 604/192, 198, 604/263, 162, 156

[56] References Cited

U.S. PATENT DOCUMENTS

| | | | |
|---|---|---|---|
| 3,612,051 | 10/1971 | Arce | 128/215 |
| 3,820,652 | 6/1974 | Thackston | 604/193 X |
| 4,417,887 | 11/1983 | Koshi | 604/162 |
| 4,425,120 | 1/1984 | Sampson et al. | 604/198 |
| 4,642,099 | 2/1987 | Phillips et al. | 604/198 X |
| 4,702,739 | 10/1987 | Milorad | 604/198 |
| 4,738,663 | 4/1988 | Bogan | 604/198 |
| 4,923,446 | 5/1990 | Page et al. | 604/198 |
| 5,057,089 | 10/1991 | Greco | 604/198 |

FOREIGN PATENT DOCUMENTS

| | | |
|---|---|---|
| 0022977 | 1/1981 | European Pat. Off. . |
| 0518416 | 12/1992 | European Pat. Off. . |
| 1007513 | 5/1952 | France . |
| 2616331 | 12/1988 | France . |
| 1022758 | 1/1958 | Germany . |
| WO9219296 | 11/1992 | WIPO . |

*Primary Examiner*—Sam Rimell
*Assistant Examiner*—Robert V. Racunas
*Attorney, Agent, or Firm*—Sughrue, Mion, Zinn, Macpeak & Seas, PLLC

[57] ABSTRACT

An auto-injector for a medicament prefilled syringe, having a head at one end and fitted with a needle at the other end, the auto-injector incorporating a first device D1 which makes automatic the needle penetration into the user's body and controls a second device D2 which performs the medicament injection. The first device includes: a cylindrical body (1) formed for receiving a syringe (4) and provided at its upper end with a collar forming a seat suitable to bear the head of the syringe, and a sliding tubular element or slider (5) concentric to the body and adapted to slide on a cylindrical surface of the body. One of the body (1) and slider (5) is formed with a bevelled projection and the other of the body (1) and slider (5) is formed with a shoulder (11). A resilient ring (9) is arranged in such a way that ring (9) prevents the reciprocal movement of body (1) and slider (5) thus maintaining the latter in such a position to cover the entire needle (10) of the syringe. The resilient ring is designed for spreading when a predetermined force exerted on the slider is reached and so allowing reciprocal movement of body and shoulder, the slider reaching a position in which the needle is uncovered and penetrates into the user's body. The slider is fitted with an appendix disposed for releasing a triggering device on the second device when the reciprocal movement is completed.

12 Claims, 8 Drawing Sheets

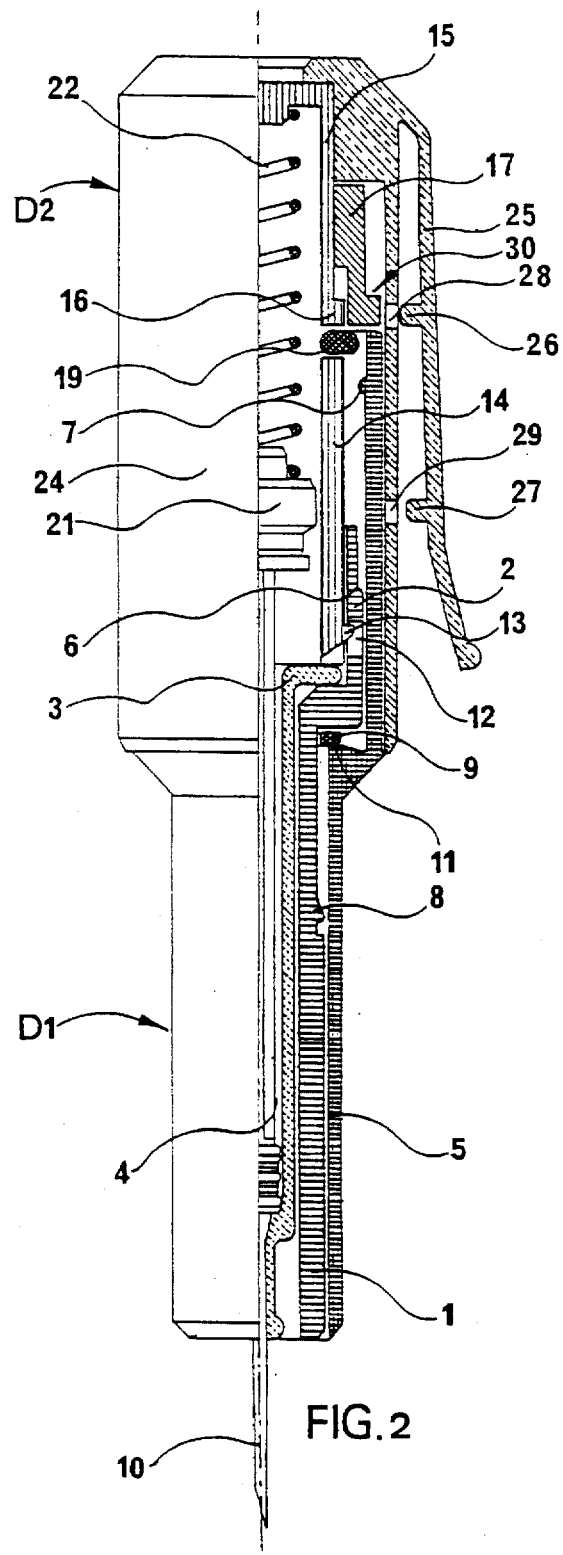
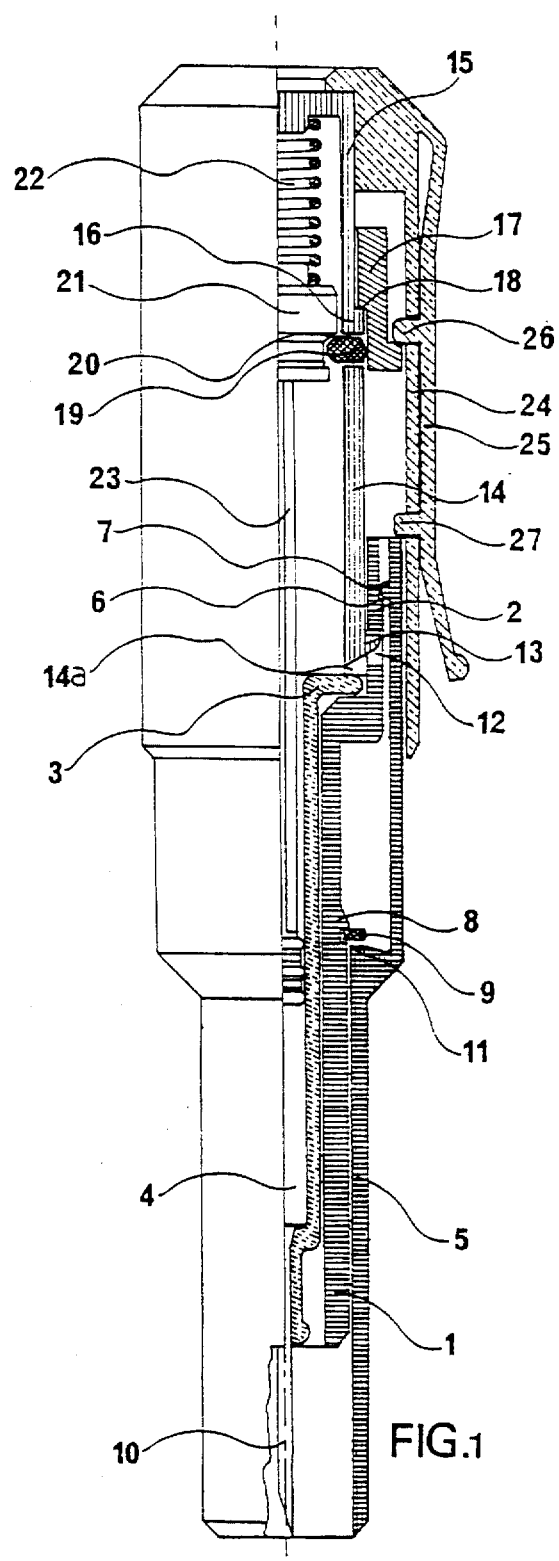

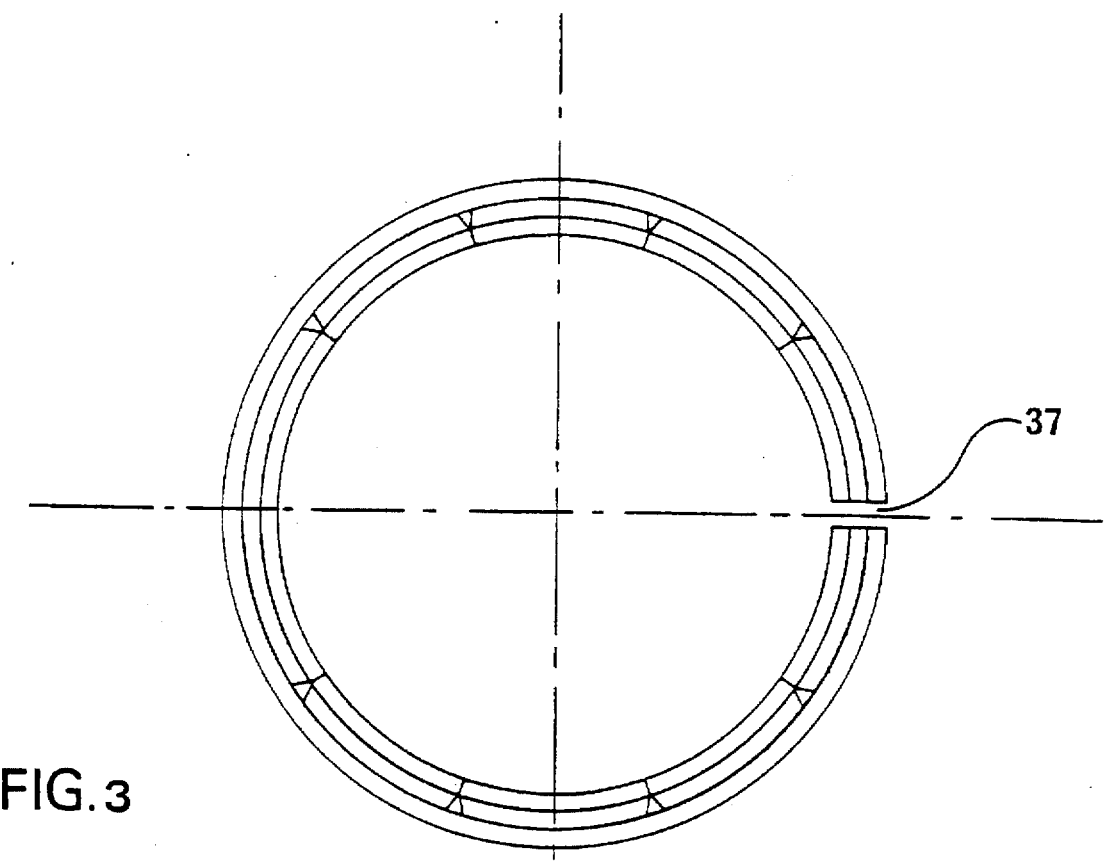
FIG.3
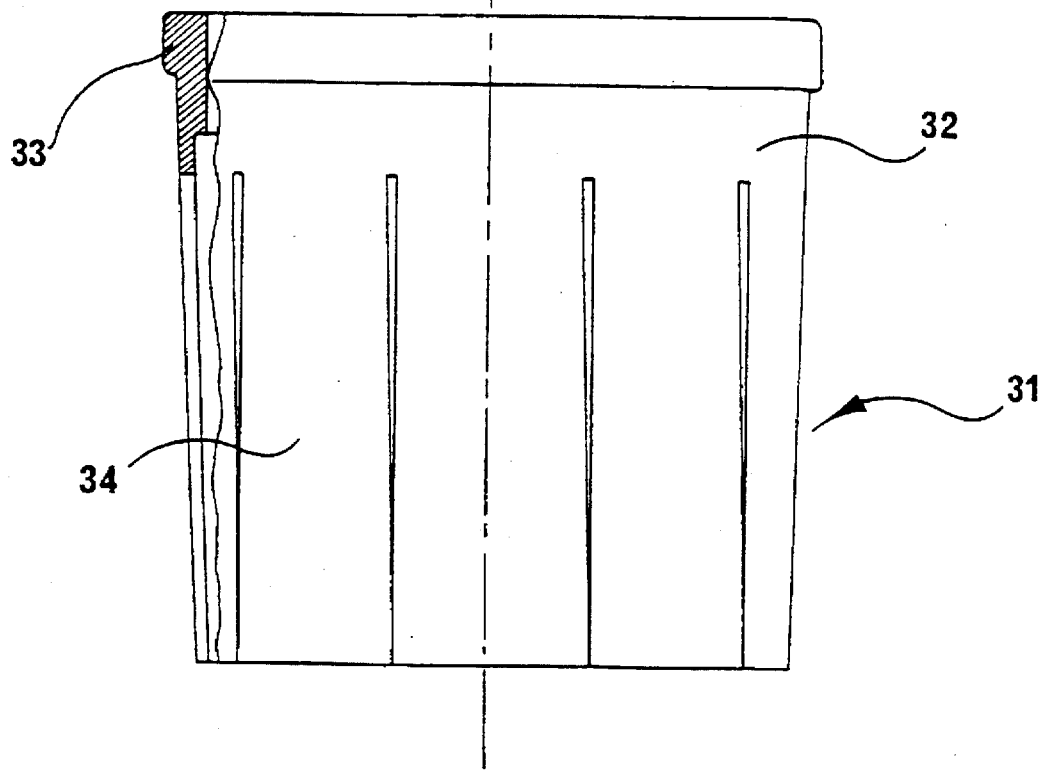

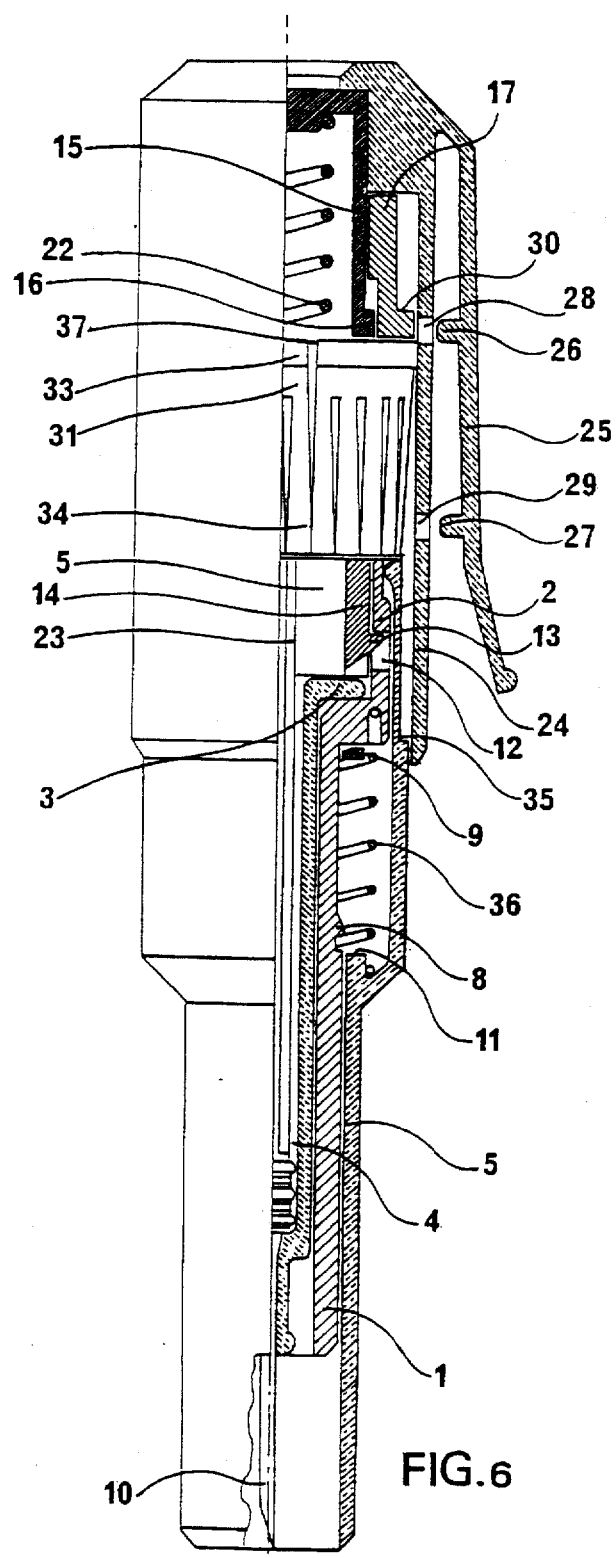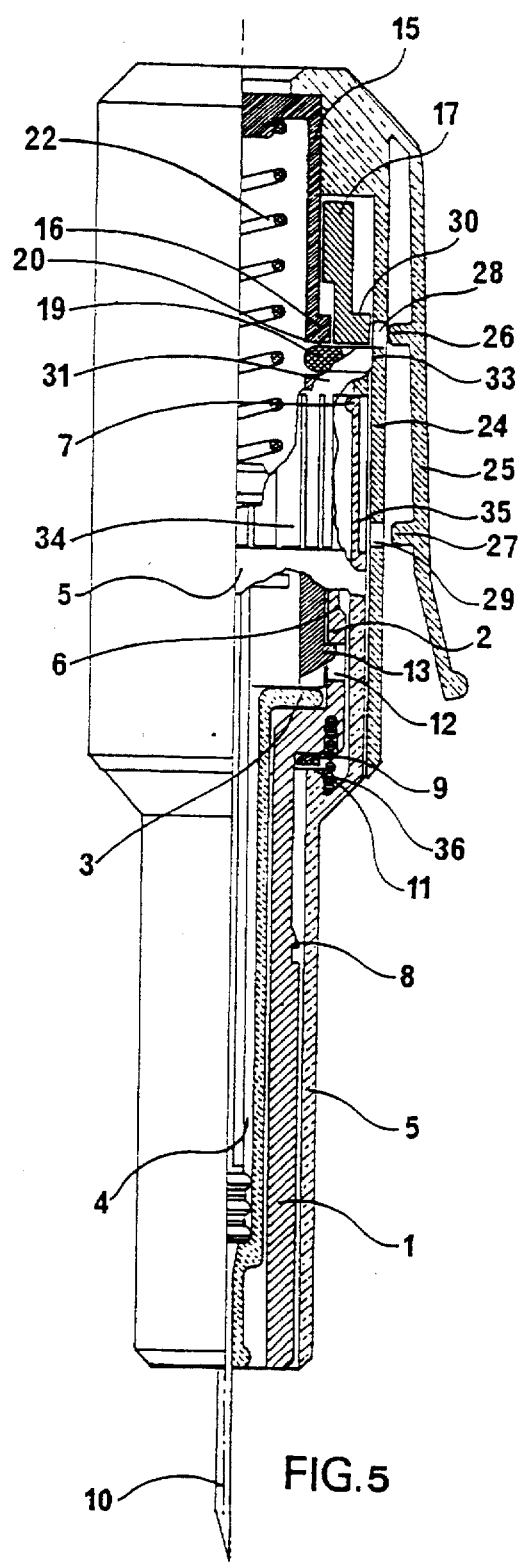

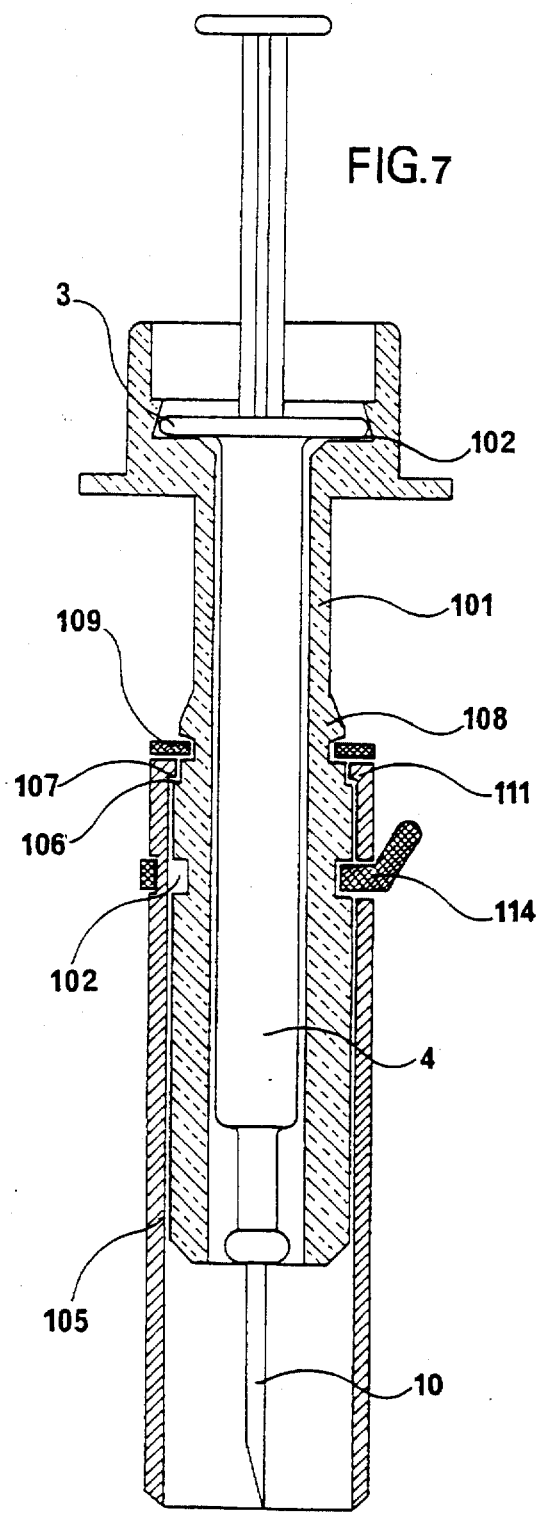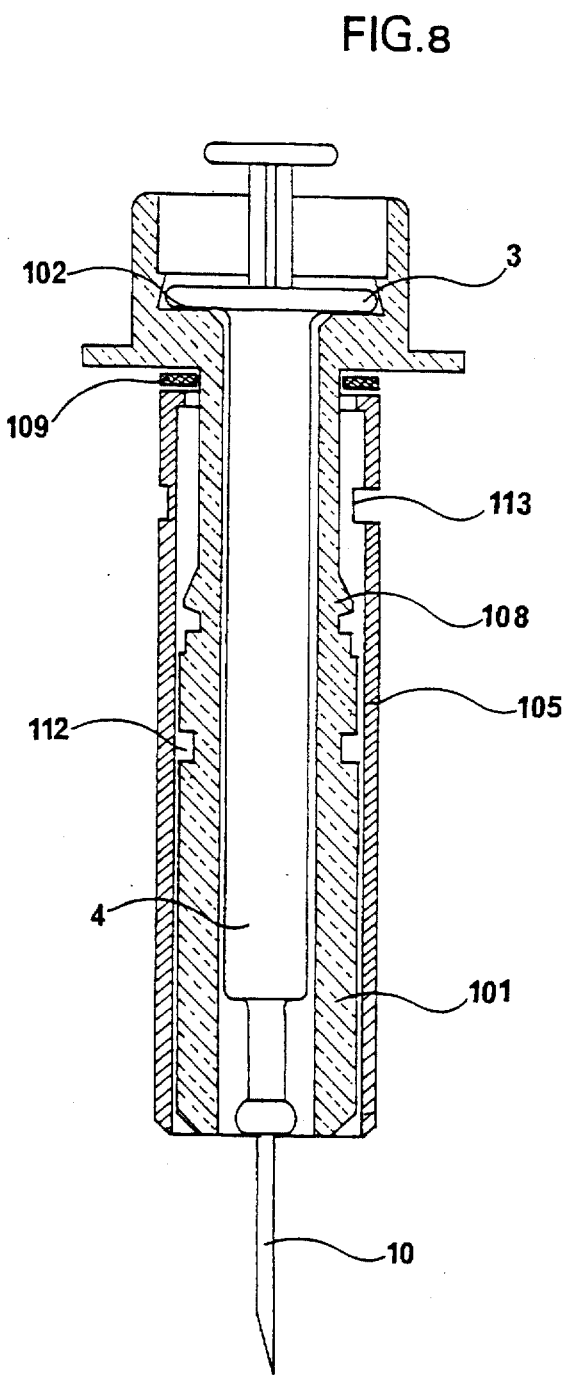

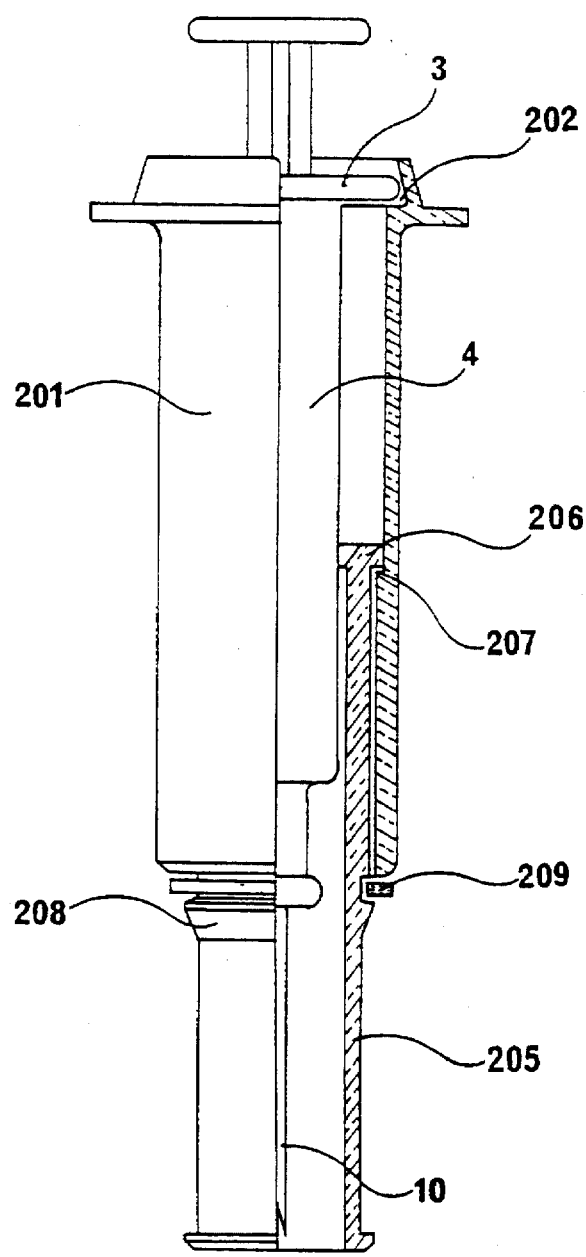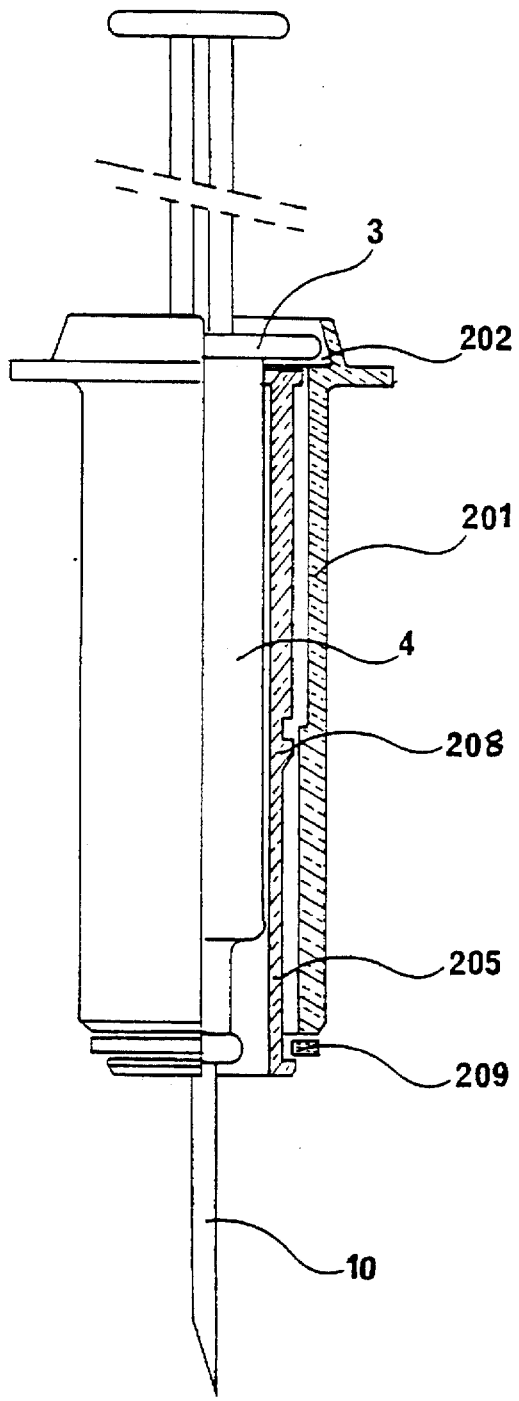

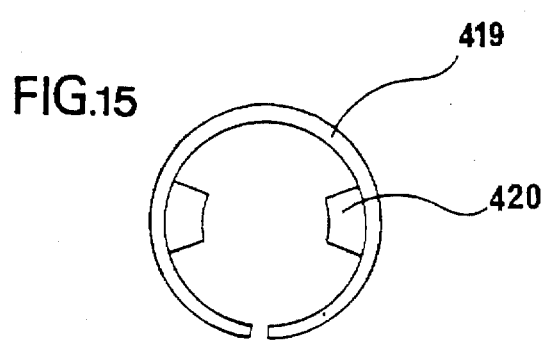
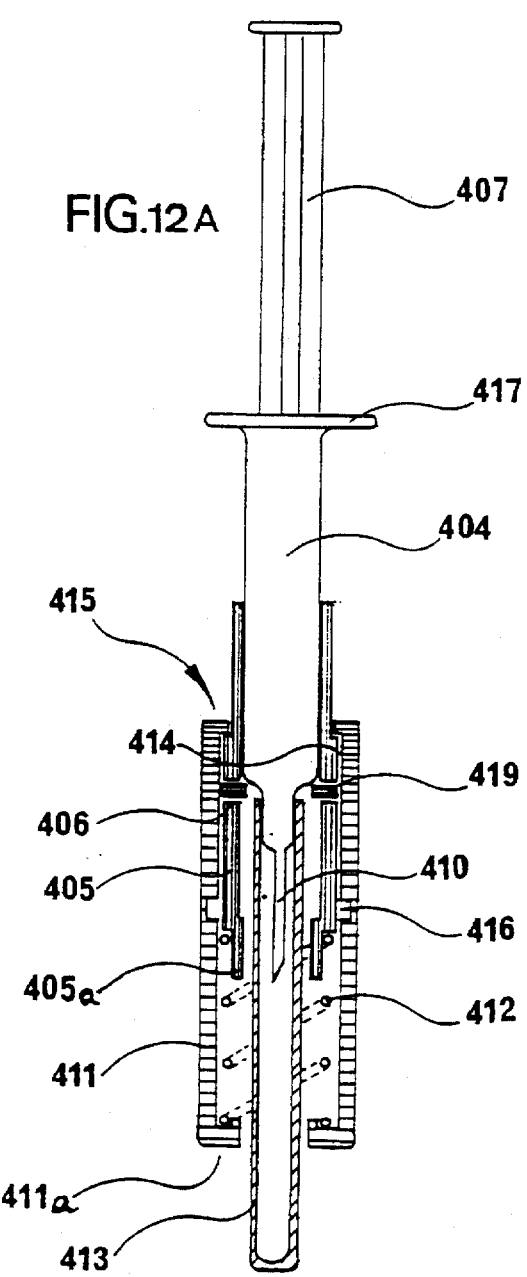
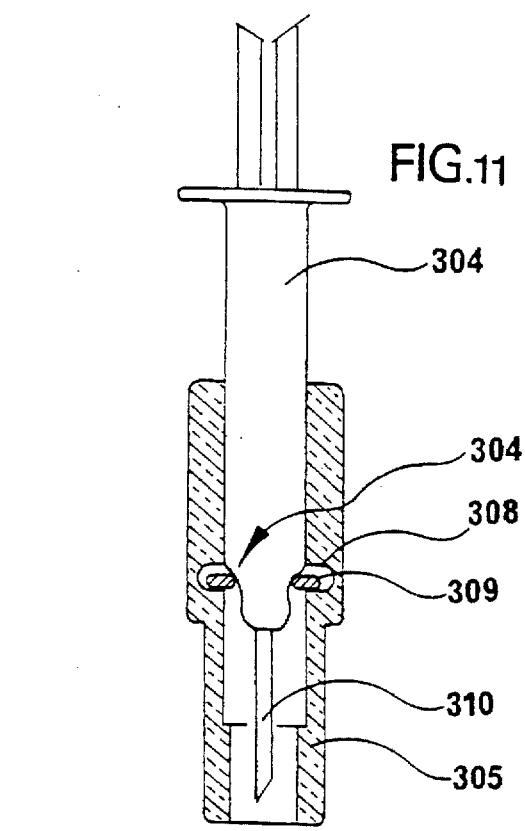
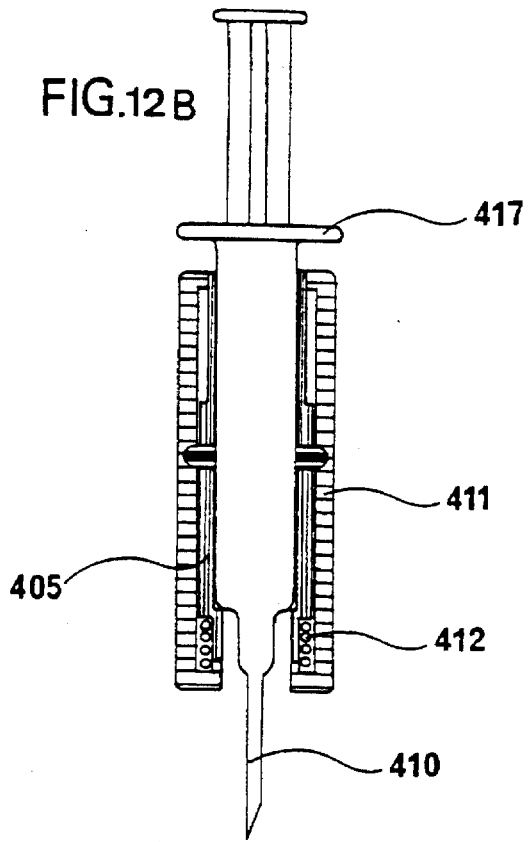

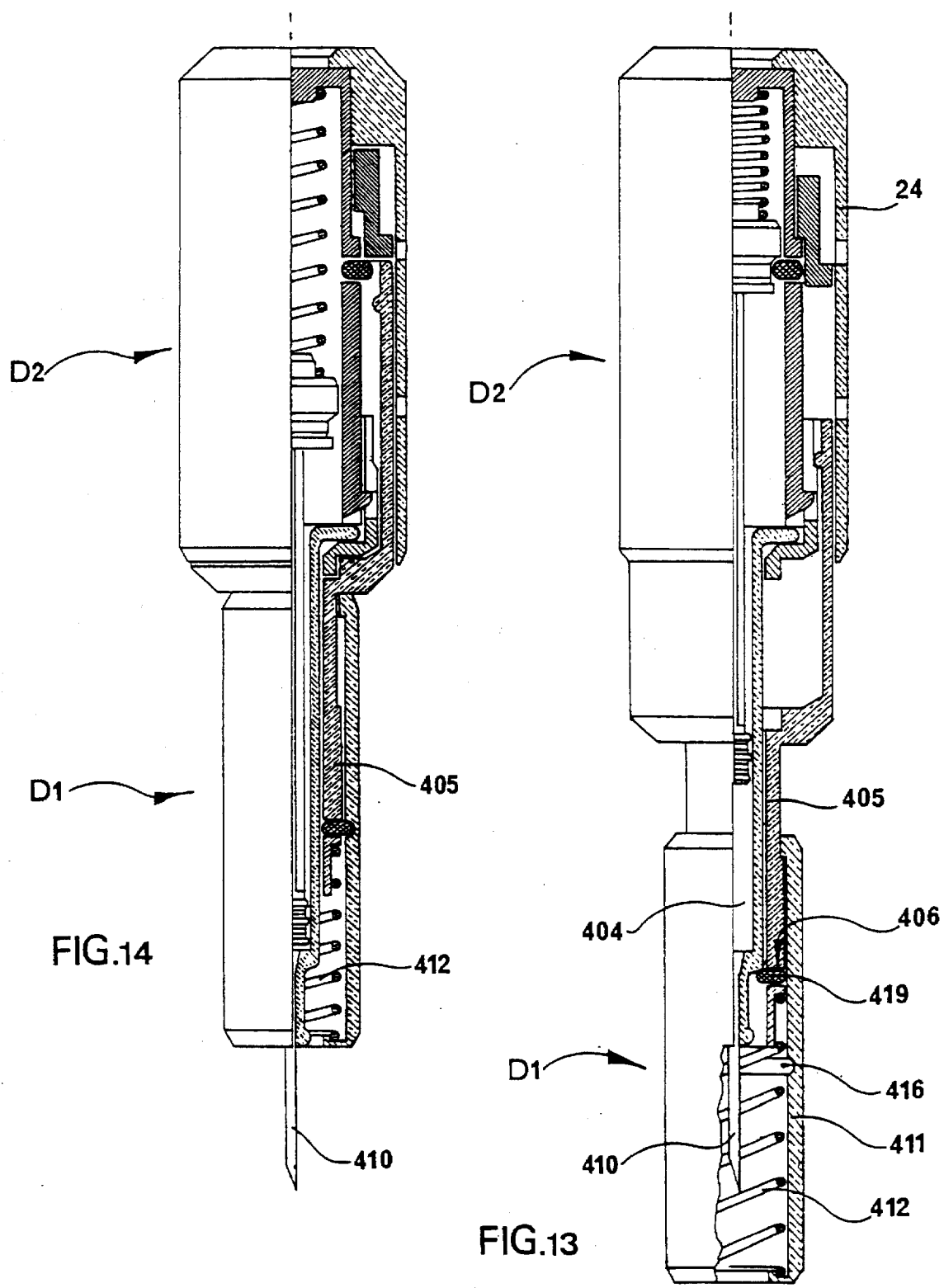

DISPOSABLE AUTO-INJECTOR FOR PREFILLED SYRINGES

The present invention relates to an auto-injector for prefilled syringes incorporating a first device which makes automatic the needle penetration into the user's body and controls a second device which performs the medicament injection with the result of having the medicament injection beginning only after the complete needle penetration thereby avoiding any medicament delivery at a non-desired depth or site.

A further object of the invention is to provide an effective and automatic protection of the needle after the injection, avoiding any risk of accidental needlestick injury.

A third object of the present invention is to provide an automatic disposable device for prefilled syringes just intended to aid, by making it automatic, the needle introduction into the patient's body and requiring the manual injection of the medicament by means of operating as usual the syringe piston.

In the pharmaceutical field, in order to facilitate certain medicament delivery by means of intramuscular or subcutaneous injections, specific automatic devices or auto-injectors have been developed.

These devices, available either as disposable or reusable versions, usually contain a syringe filled with the medicament and thanks to the action of a stressed spring which is snap released in response to determined actuating procedures they cause the forward movement of the syringe, and therefore the needle penetration into the patient's or user's body, and, at the same time, the medicament injection. Such a device is disclosed in WO 92/19296.

One of the main problems showed by these devices is caused by this commonly used working principle.

In fact the stressed spring, when released, directly transmits its thrust against the piston of the syringe and as the forward movement of the latter, and therefore the needle penetration, offers a lower resistance than the one offered by the piston movement into the syringe to cause the liquid expulsion, the two actions occurs in a sequence.

However, in practice, the thrust exerted by the spring on the syringe piston causes a certain medicament outlet from the needle since the beginning of the thrust and therefore when the needle is not yet penetrated or has not reached the desired depth.

This situation could cause, in the use of certain medicaments, like calciheparine, whose depth of delivery is particularly important, undesired effects and in particular persistent and large haematomas.

Another problem often existing in the use of these devices depends from the need to cover the needle with a protective cap after the injection. This causes the risk of accidental needlestick injuries while placing the cap or the possibility that, through negligence, the auto-injector is discarded without a needle protection in case the cap is not replaced.

In both cases the risk of contracting an infection is evidently high.

Further problems generally related to the existing auto-injectors depend from difficulty of use, high costs or the possibility of actuation when the device is not correctly placed against the user's or the patient's body.

For this reasons, it has appeared of interest the development of a disposable instrument, or auto-injector, of great simplicity and low cost incorporating a first device able to perform the automatic and painless needle penetration into the user's body combined with a second device, controlled by the first one and actuated only when the needle penetration has been completed, which performs the medicament injection, thus eliminating any possibility of medicament delivery at an undesired depth or site.

According to the invention, there is provided an auto-injector for a medicament prefilled syringe, having a head at one end and fitted with a needle at the other end, said auto-injector incorporating a first device which makes automatic the needle penetration into the user's body and controls a second device which performs the medicament injection, said injection being controlled by a second trigger means, said first device comprising a sliding tubular element or slider concentric to said syringe, and adapted to be connected to said syringe by a first trigger means, in a position in which it covers said needle, said trigger means being releasable when applying a predetermined force on said syringe when said slider is placed against user's body, said slider being fitted with an appendix disposed for releasing said second triggering means on said second device when said reciprocal movement is completed with the result of having the medicament injection beginning only after the complete needle penetration avoiding any medicament delivery at not desired depth or site.

The above with the further characteristic of providing an automatic, not reversible, covering and protection of the needle at the end of the injection avoiding therefore any risk of needlestick injury.

A further object of the invention is to provide an aid to the injection of those medicament of low price, not able to stand the cost of a complete auto-injector, or of those medicaments whose eventual delivery in a vein is not desired, in which case a slight manual pull on the syringe piston is required to check that the needle has not reached a vein.

This object can be achieved by providing a device for the automatic and painless introduction of the needle in the patient's body which can be used alone, without the automatic medicament injector, offering therefore a significant aid to the user as the needle introduction represents one of the main technical and psychological problems in giving an injection.

Said auto-injector comprising a device, for the automatic and painless introduction of the needle into the patient's or user's body, adapted to receive a prefilled syringe having a head at one end and fitted with a needle at the other end, said device including a tubular syringe carrying body provided with a lower tubular portion containing the syringe up to the base of the needle and with an upper protruding larger collar for the coupling with the head of said syringe, said body also carrying outside a sliding tubular element or slider provided with two bores, the smaller of which corresponding to the diameter of the body portion containing the syringe and the larger to the collar of the syringe carrying body, bores joined by a circular shoulder formed in such a position that the distance between said shoulder and the base of the body collar correspond at least to the needle length so that at rest position the slider covers the needle while when completely slided fully uncovers the same. Said syringe carrying body further provided at a suitable position with an annular bevelled projection forming together with the shoulder on the slider, a seat which holds a resilient slit detent ring therefore preventing the upward movement of the slider over the syringe carrying body. Syringe carrying body whose enlarged collar holds and locks the open side of a hollow cylindrical element, casing of the medicament injection device, having the opposite end closed and of reduced outer diameter carrying a tubular sliding control sleeve suitable to force a resilient expansible detent ring, operating in a circular slotted groove, formed on the hollow casing, to inwardly protrude, through said slots, and retain a piston urged by a stressed spring bearing against the closed end of the hollow casing, piston also resting against the head of the syringe piston. Said casing also bearing a tubular protection element which covers the control sleeve and the whole unit unto the upper edge of the needle penetration device, and is provided with two holes suitable to receive two pins, part of a safety plate element, which rest against the control sleeve and the edge of the needle device slider preventing their upward movement.

The above is arranged in such a way that during the injection, with the bottom of the needle device slider bearing against the user's body, the thrust exerted by the user on the unit and transmitted to the syringe carring body must reach in order to allow the needle coming out, a force enough high to win the resistance of the resilient detent ring, of the needle device, to enlarge; enlargement which allows said ring to escape its seat and to snap over the annular projection formed on the syringe carrying body, thus instantly releasing all the energy accumulated in the user's hand and causing the needle device slider to snap upward uncovering the needle which therefore penetrates with predetermined optimal speed and force depending on the mechanical and elastic characteristics of the needle device detent ring.

At the end of its upward movement, and therefore only when the needle penetration is completed, the upper edge of the slider reaches the injection device control sleeve, forcing it to move upwards and therefore allowing the free expansion of the injection device expansible detent ring and the release of the injection device piston which, under the thrust of the stressed spring, pushes the syringe piston and causes the medicament outlet.

Said auto-injector can also be provided with an automatic safety needle protection, automatically and irreversibly covering the needle at the end of the injection consisting of an elastic sleeve, provided with a full longitudinal slit allowing its enlargement, having an upper portion of cylindrical shape, provided with an external and slight annular projection, and a lower and thinner portion of frusto-conical shape provided with slits forming longitudinal segments of high flexibility.

Said lower segmented portion is inserted over a seat, formed on the upper portion of the needle device slider, whose diameter is such to cause the elastic sleeve to enlarge, thanks to its longitudinal slit and to the flexibility of its lower segmented portion, in such a way that the slight outer annular projection of the elastic sleeve exert a thrust on the internal walls of the protection cover of the auto-injector enough light not to obstacle the snap upward movement of the needle device slider, but higher than the one exerted by its lower segmented portion against the seat on the same slider, which is very light due to the high flexibility of said segments.

The above is arranged in such a way that, also thanks to the thrust of a light return spring, placed between the outer base of the collar of the syringe carrying body and the shoulder formed on the needle device slider, at the end of the injection, and after removing the auto-injector from the patient's body, the needle device slider return to its starting position and cover the whole needle while the elastic sleeve thanks to its higher friction against the protection cover walls remains in its position and, being slightly shorter than the stroke of the slider, completely get out from the seat made on the same, returning therefore to its original smaller diameter which is such to prevent the upward return of the slider thus irreversibly locking it in a needle protection position.

Finally, the invention provides an automatic and painless needle penetration device, allowing a manual medicament injection, the device comprising a syringe carrying and fixing body, a slider and a first trigger means placed between said body and said slider.

Such a device is disclosed in U.S. Pat. Nos. 4,702,739 and 3,612,051. However, the trigger means of these devices are complicated and thus expensive to manufacture.

According to the invention, there is provided an automatic needle penetration device for a medicament prefilled syringe, having a head at one end and fitted with a needle at the other end, said device comprising a syringe carrying body containing the syringe up to the base of the needle, provided with a seat for receiving and lock said syringe head, and a sliding element or slider of tubular shape slidable along said body, said slider when ready for use covering completely the needle end, characterized in that one of said body and said slider is provided with an annular bevelled projection, suitable to form together with the edge of one of said body and said slider, a seat for a first trigger means, said first trigger means comprising a detent slit ring having one single slit. A detent slit ring having only one slit is easy and cheap to realize and allows to define easily and cheaply the predetermined optimal speed and force necessary to release said trigger means, these optimal speed and force depending on the mechanical and elastic characteristics of the detent ring.

The accompanying drawings show the invention in different scales, by way of non limiting examples.

In the drawings:

FIG. 1 is an axial partly sectional view of the auto-injector being concerned at rest position before the removal of the safety pins;

FIG. 2 is an axial partly sectional view with the auto-injector at the end of the injection;

FIG. 3 is a plant and side detail view of the elastic sleeve of the needle protection system;

FIG. 5 is a view similar to FIG. 2 with the auto-injector incorporating the needle protection system after the injection but just before the automatic needle protection occurs;

FIG. 6 is a view similar to FIG. 5, but with the automatic needle protection occured;

FIG. 7 is an axial partly sectional view of the automatic needle penetration device to be used alone before the use;

FIG. 8 is an axial partly sectional view of the automatic needle penetration device as in FIG. 7 after the actuation;

FIG. 9 is an axial partly sectional view of a possible detail modification to the automatic needle penetration device to be used alone, before the actuation;

FIG. 10 is a view similar to FIG. 9 showing the modified device after the actuation;

FIG. 11 is a vertical cross section of a simplified device according to the invention;

FIG. 12B is a view showing the device of FIG. 12A after having completing an injection;

FIG. 12A is a view similar to FIG. 11, showing a device with a safety needle protection;

FIG. 13 is a view partly in elevation partly a section of a further embodiment of the invention, ready for use;

FIG. 14 is a view of the device of FIG. 13, after use, but before taking the device away from the user's body; and FIG. 15 is a plan view of an example of a slitted elastic counteracting ring used in the device of the present invention.

Figure 4:
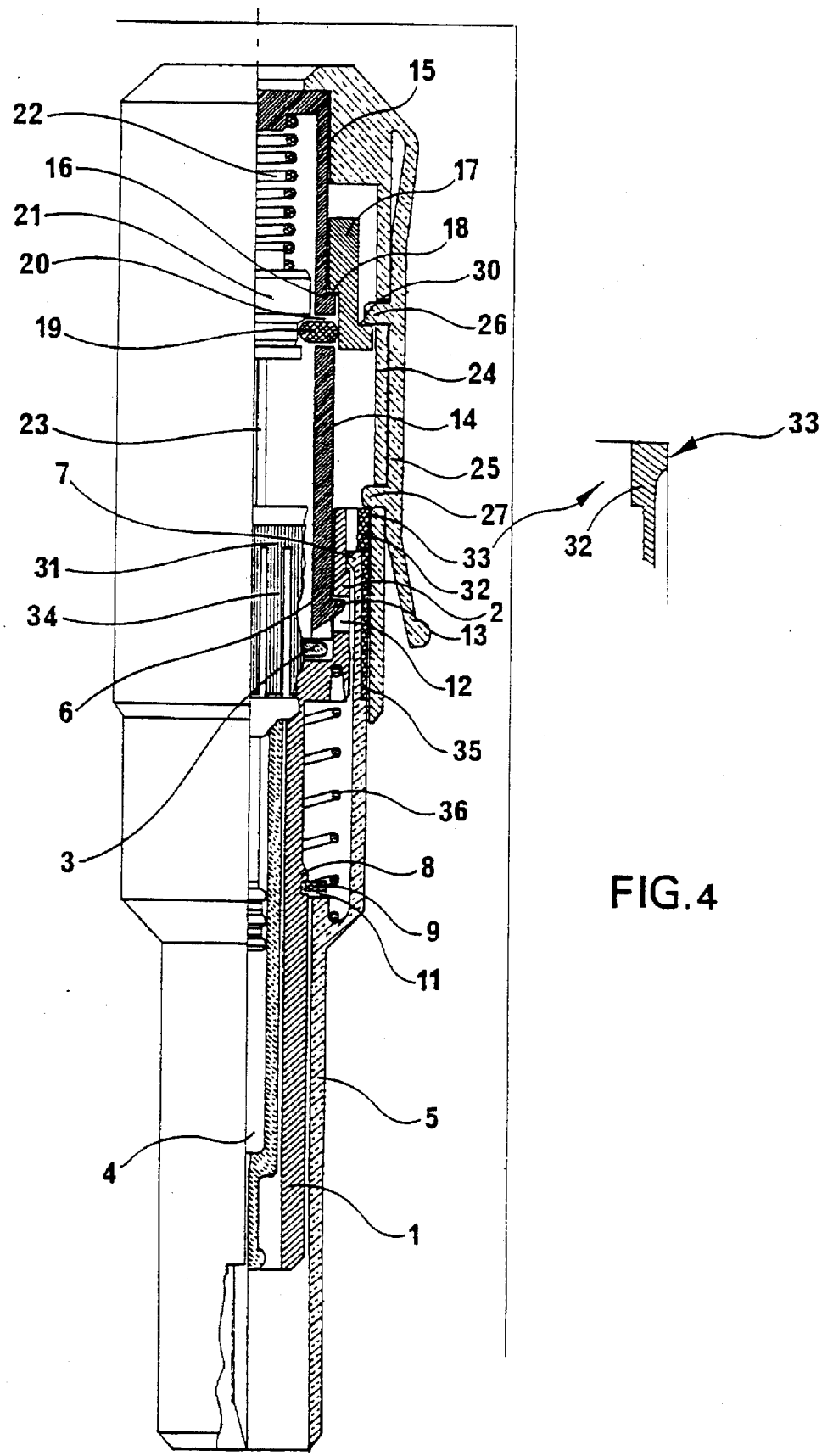
FIG. 4 is a view similar to FIG. 1 with the auto-injector incorporating the needle protection system before the use.

For the clarity of the disclosure, some parts of the described devices are indicated with high, upper, low, lower, etc., which are construed to be read on the Figures, without limiting effect. The devices may evidently be used in any orientation.

As clearly shown in FIG. 1, the auto-injector according to the present invention comprises a device D1 for the automatic and painless introduction of the needle into the patient's or user's body consisting of a cylindric tubular body 1 provided at its upper end with a larger collar 2 forming a seat suitable to bear the rear part or head 3 of a syringe 4 provided as usual with radial planes. Said syringe carrying body 1, which contains the syringe 4 from the base of the needle 10, is fitted outside with a sliding tubular element, or slider 5, provided with two bores, the smaller of which corresponding to the diameter of the body portion carrying the syringe 4 and the larger to the collar 2 of said syringe carrying body, joined by a shoulder 11 formed in such a position that the distance between said shoulder 11 and the base of the body collar 2 corresponds at least to the length of the needle 10 so that at the rest position, shown in FIG. 1, the slider 5 covers the whole needle 10, while when completely slid back fully uncovers the same as shown in FIG. 2. The collar 2 of the syringe carrying body 1 being provided with an annular retaining shoulder 6 acting against a corresponding annular projection 7 formed in the larger bore of the slider 5 in such a way that the two elements, body 1 and slider 5, can reciprocally slide without having the possibility to separate from each other.

Said syringe carrying body 1 is further provided, at a suitable position, with an annular bevelled projection 8 forming together with the shoulder 11 of the slider 5 a seat which holds a resilient slit detent ring 9.

The whole is arranged in such a way that said detent ring 9 prevents the reciprocal movement of body 1 and slider 5, thus maintaining the latter in such a position to cover the entire needle 10.

The collar 2 is fitted with coupling means for securing the automatic needle penetration device D1 and the medicament injector device D2. These coupling means comprise slots 12, intended to hold, inserted and locked, the open end of casing 14 which is a hollow cylindrical element, housing the medicament injector device. Said casing is fixed to the upper end of body 1 and for achieving that is provided with retaining teeth 13 inserted into said slots 12 of the collar 2. Casing 14, whose lower edge bears against the upper part 3 of the syringe 4, so locking it, and has its opposite portion 15 with closed bottom and of a reduced outer diameter, so forming a shoulder 16, setting the position of a control sleeve 17. Said sleeve 17 is formed with a corresponding abutment 18, which can engage said shoulder 16 and is mounted for sliding over said reduced diameter portion 15 between an upper position (FIG. 2) and a lower position (FIG. 1) in which it internally compresses, keeping it closed, a resilient expansible slit ring 19, provided with detent teeth, operating into a circular groove 20, formed on the casing 14, provided with slots through which said detent teeth of the ring 19 inwardly protrude inside the bore of casing 14 and retain a piston 21, axially sliding into said bore, urged by a spring 22 compressed between the closed bottom of said casing 14 and the same piston 21 which rests with its opposite face against the piston 23 of the syringe 4. An embodiment of such a ring 19 is shown on FIG. 15.

The auto-injector further comprises a tubular protection cover 24, fixed to the upper end of the casing 14, covering the control sleeve 17 and the whole auto-injector down to the upper edge of the slider 5, provided with a flexible radial arm 25 carrying two safety pins 26 and 27 intended to be inserted into two corresponding holes 28 and 29 formed into the protection cover 24 in such a position that, when inserted, and with the auto-injector not actuated, the lower pin 27 rests against the edge of the slider 5 while the upper pin 26 rests against a suitable annular shoulder 30 formed on the control sleeve 17, preventing their upper movement and acting therefore as a safety device.

In order to perform the injection, it is necessary, after removing the safety pins 26 and 27 by pulling the free end of the flexible arm 25, to position the lower end of the slider 5 against the part of the user's or patient's body where the injection is to be given and to apply a push or a pressure on the protection cover 24 towards the patient's body.

This pressure, through the casing 14 and the upper part 3 of the syringe 4, is transmitted to the syringe carrying body 1 whose forward movement is opposed by the resilient detent ring 9 bearing against the annular bevelled projection 8, until when it is reached a pressure, or force, high enough to force the slit detent ring 9, to expand, under the thrust transmitted by the shoulder 11 of the slider 5, and to snap over the annular projection 8.

This action causes a predetermined energy accumulation in the hand of the user, depending from the mechanical and elastic characteristics of the slit detent ring 9, which is instantly released when the slit ring 9 snaps over the annular projection 8, causing a forward snap movement of the body 1 and of the whole auto-injector including the syringe 4 together with a rearward movement of the slider 5 over the body 1 and inside the protection cover 24.

This movement of the slider 5 instantly uncovers the needle 10, which is then free to penetrate at predetermined and optimal speed and force, and causes the upper edge of the same slider 5 to reach, at the end of the needle penetration stroke, the control sleeve 17 and remove it from its position allowing therefore the expansible detent ring 19 to expand.

This expansion releases the piston 21 which, under the thrust of the stressed spring 22, now released, pushes the syringe piston 23 causing the medicament outlet and delivery as shown in FIG. 2, delivery which begins only when the needle is fully and correctly penetrated and therefore exclusively at the desired depth and site.

The auto-injector object of the present invention can also be provided with a device which forces the slider 5 to automatically return to its original position fully covering and protecting the needle 10 made in such a way to cause an irreversible lock of the slider 5 in this position.

As clearly shown in Figures from 3 to 6, the auto-injector can be provided with an elastic sleeve 31, better shown in FIG. 3, provided with a full longitudinal slit 37 allowing it to enlarge increasing its diameter and acquiring a tension to return to its original shape and diameter. The sleeve is formed with an upper cylindrical portion 32, provided with an annular projection 33, and with a lower portion of larger internal diameter, and therefore with thinner walls, of frusto-conical shape provided with longitudinal slits dividing it into highly flexible longitudinal segments 34.

Said elastic sleeve 31 is inserted, as shown in FIGS. 4 and 5, with its lower and segmented portion over a suitable seat 35 formed as a diameter reduction on the external walls of the upper portion of the slider 5, said seat 35 having such a diameter to cause the elastic sleeve 31 to enlarge thanks to its longitudinal slit 37 and to the high flexibility of its segments 34. In this position the annular projection 33 formed on the elastic sleeve 31 is brought to strict and direct contact with the walls of the protective cover 24 and exerts against the same a predetemined thrust.

The device is further completed by a light return spring 36 retained between a seat formed on the outside base of the collar 2 of the syringe carrying body 1 and another seat suitably made on the shoulder 11 of the slider 5.

During operation, the force exerted by the annular projection 33 against the walls of the protection cover 24 is light enough not to prevent the snap rearward movement of the slider 5, but high enough to cause a friction force against said cover 24 which is greater than the one made by the segments 34 against the seat 35 of the slider 5, friction force which is very light due to the high flexibility of said segments 34.

This causes, when the injection is completed and the auto-injector is removed from the patient's body, the slider 5, pushed by the light returned spring 36, to return to its starting position covering the whole needle, while the elastic sleeve 31, thanks to the higher friction of its annular projection 33 against the protection cover 24, remains in the position shown in FIGS. 5 and 6, and as its length is slightly shorter than the stroke of the slider 5, completely get out from the seat 35 of the slider 5.

This allows the elastic sleeve 31, no longer enlarged, to return to its original smaller diameter whose size is such to prevent its return over the seat 35 and therefore the rearward movement of the slider 5 thus irreversibly locking it into a needle protection position.

Instead of a friction against the inner wall of the cover, projection 33 which may be inside the elastic sleeve 31 may provide a friction against the outer wall of casing 14, the segmented portion of the elastic sleeve then being contracted, inside the inner wall of the upper portion of slider 5, instead of being expanded around its external wall.

According to the invention, the system can consist just of the automatic needle penetration device which in this case comprises, as shown in FIGS. 7 and 8, a syringe carrying body 101 provided with a seat 102, instead of a collar 2, suitable to retain and lock the end of a syringe 4, said body 101 having outside inserted a sliding element or slider 105, of tubular shape and with only one bore provided at its upper end with a retaining annular projection 107 acting against a correspondent shoulder 106 formed on the syringe carrying body 101. Body 101 is also provided, as above described, with an annular bevelled projection 108 suitable to form, together with the upper edge 111 of the slider 105, a seat for a detent slit ring 109.

The above device being also provided with a safety system consisting of a flexible and extractable element 114 shaped as an open ring, with a radial protrusion, operating in the non actuated device, shown in FIG. 7, as a key into an opening 113, provided on the slider 105 and at the same time into a corresponding annular groove 112 formed on the body 101 in such a way to lock the two elements in order to prevent any accidental actuation of the device.

In the use, the automatic needle penetration device, after removing the safety element 114, works exactly as the corresponding device part of the complete auto-injector.

FIGS. 9 and 10 show a possible modification to the needle penetration device, to be used alone, still within the basic principle of the invention.

In this configuration, the slider 205 is inserted inside the body 201, instead of outside, and the annular projection 208 is formed on the slider 205 instead of on the syringe carrying body 201 whose lower edge now represents the shoulder forming, together with said projection 208, the seat which holds the resilient slit detent ring 209.

The working concept remains unchanged on respect of the basic embodiment with the advantage of allowing an easier assembling process.

In the device represented on FIG. 11, the syringe 304 has a form adapted for being placed directly in the slider 305, see particularly at the lower end of the syringe near the base 304a of needle 310, so that there is no need of a syringe receiving body, i.e. syringe and body are forming only one piece. The inner wall of the slider 305 is formed with a circular groove 308 in which is disposed a resilient slit ring 309. Said groove 308 is large enough to allow the slit ring to expand whereby allowing the syringe to move down under a predetermined force. The operation of this device is the same as for the embodiment of FIGS. 7 and 8.

The device of FIGS. 12A and 12B includes a protection of the needle after the injection, so avoiding any risk of accidental needlestick injury.

In the device of FIG. 12A, the syringe 404 is mounted in a slider 405 with a slit ring 419 such as represented on FIG. 15, disposed in a groove 406 formed in the outer wall of said slider, and provided with slots allowing the teeth 420 to protrude inside the slider 405.

A thimble 411 is fitted over slider 405 and is biased away from the syringe head by means of a spring 412, so as to cover completely the needle 410, when the syringe is depressed in the slider and has its position defined by a shoulder 414 on the slider and a collar 415 at the upper end of said thimble.

A circular groove 416 is formed on the inner wall of the thimble 411, for allowing the ring 419 to expand when it is coming in front of said groove 416, so allowing the teeth 420 to retract from the inside of said slider and so allowing reciprocal movement of the syringe in the slider.

In operation, at the start position such as represented on FIG. 12A, after having taken away the needle protective cap 413, the bottom 411a of the thimble is positioned against the part of the body where the injection is to be given and a normal pressure is started on the syringe collar 417 towards the user's body.

In this situation the syringe is kept still, on respect of the tubular slider 405, due to the locking action of the detent teeth of the expansible ring 419 protruding, through the slots of the groove 406, against the front of the syringe barrel, ring 419 which cannot expand as retained by the internal walls of the cylindrical thimble 411.

Therefore said pressure and the consequent downward movement are transferred to the slider 405, which movement requires to overcome the tension of the cylindrical counter spring 412.

The preset force needed to win said tension causes an accumulation of a predetermined energy in the hand and the arm of who is giving the injection.

This energy raises until the syringe unit approaches the position in which ring 419 can expand in groove 416.

The continuation of the movement of the syringe 404 and therefore of the slider 405 will take the expansible resilient ring 419 to the level of said circular groove 416 where it will expand under the pressure of the edge of the syringe barrel.

This expansion of the resilient ring 419, which occurs as an instant snap, causes the following two consequences:

the first is that the resilient ring 419 gets a position where it is partly inserted into the expansion groove 416 and partly into the circular groove 406 on the slider 405, which locks the latter and therefore the upward thrust of the counter spring 412;

the second is that the expansion of the resilient ring 419 eliminates the axial detent function of its teeth against the syringe 404, which being no longer retained and no longer subjected to the counteraction of the spring 412, snaps forward, instantly releasing the energy accumulated in the hand and arm Of who is giving the injection and allowing a needle introduction and penetration which are rapid, controlled and painless. The device is then in the position FIG. 12B.

At this point the medicament can be injected as usual by pressing the plunger rod 407.

The tension of the cylindrical counter spring 412 is preset and fixes both the speed and the force of the needle penetration allowing therefore a reproducible and optimal action which is independent from the experience and the skill of who is giving the injection. The accumulation of energy in the hand of the user may also result of the stiffness of the ring, essentially, or in addition with the strength of the spring.

The control of the penetration depth of the needle 410 into the user's body is assured by the proper length of the lower portion of the cylindrical thimble 411.

After the injection is completed and the device unit removed from the user's body, a traction is applied on the syringe 404, while holding still the thimble until the lower thinner part of the syringe passes in front of ring 419, which then contracts in the groove 406 and under the syringe.

This releases the spring 412 which takes again the unit at the starting position in which it is possible to safely and easily replace the needle protective cap without any risk of needlestick injuries.

The device of FIGS. 13 and 14 is similar to the device of FIGS. 1 and 2, but after having been modified for receiving a needle protection system similar to the one represented of FIGS. 12. In other words, the auto-injector of FIGS. 13 and 14 is differing from the one of FIGS. 4, 5 and 6 in that the needle protection system is different. The auto-injector of FIGS. 13 and 14 includes a first device D1 which makes automatic the needle penetration into the user's body: this device is similar to the one of FIGS. 12, and the corresponding parts are marked with the same reference numbers. The syringe 404 is placed in a slider 405 and positioned by means of a slit ring 419. A thimble 411 with a groove 416 is mounted on the slider in the same way as in FIG. 12, with a spring 412. This needle penetration device operates exactly as the one of FIGS. 12: when pushing on cover 24, after having placed the auto-injector in the right place, the whole moves down, compressing spring 412 untill ring 419 is able to expand in groove 416, after what, under the effort aplied for expanding the ring, the auto-injector snaps down and provides the needle penetration.

The thimble 411 and the slider 405 are then connected by means of ring 419, projecting in both grooves 406 and 416. So the penetration of the needle causes a further upwards movement of thimble 411, carrying with it the slider 405, which release the device D2 which performs the medicament injection, exactly as described in regard of FIGS. 1 and 2. The auto-injector is then as shown on FIG. 14. After the auto-injector has been removed from user's body, the needle is covered by pulling device D1 from device D2: slider 405 and thimble 411, which are locked together by ring 419 are moved away from device D2, into a position where needle 410 is completely covered and protected.

I claim:

1. An auto-injector for a medicament prefilled syringe (4), having a head at one end and fitted with a needle at the other end and including a syringe piston (23), said auto-injector incorporating a first device D1 which makes automatic the needle penetration into a user's body and controls a second device D2 which performs the medicament injection, said first device D1 comprising:

a cylindrical body (1) formed for receiving the syringe (4), said cylindrical body being provided at an upper end with a collar forming a seat suitable to bear the head of the syringe, a slider (5) concentric to said body and adapted to slide on a cylindrical surface of said body, a first trigger means (9) arranged such that a reciprocal movement of said body and said slider is prevented, thus maintaining the slider in a position to cover the entire needle (10) of the syringe, the first trigger means being releasable when a predetermined force is exerted on said slider, thus allowing reciprocal movement of said body and said slider, said slider reaching a position whereat said needle is uncovered and penetrates into the user's body, said second device D2 comprising:

a piston (21), resting against the syringe piston (23) and urged by a compressed spring (22), a second trigger means (19), retaining said piston (21), wherein one of said body and said slider is formed with a bevelled projection and the other of said body and said slider is formed with a shoulder (11), said first trigger means (9) being partly placed between said projection and said shoulder, said slider (5) of said first device D1 being fitted with an appendix disposed for releasing said second trigger-means (19) of said second device (D2) when said reciprocal movement of said body (1) and said slider (5) is completed with the result of having the medicament injection beginning only after the complete needle penetration thereby avoiding any medicament delivery at a non-desired depth or site.

2. An auto-injector according to claim 1, wherein said second device comprises a casing (14) formed with a bore and having a lower open end and a closed upper bottom, said lower open end of said casing being fixed to the upper end of said body, (1) by connecting means (12, 13), said casing housing the piston (21) axially sliding into said bore, resting against the syringe piston (23) and urged, on its opposite side, by a spring (22), compressed between said closed bottom and said piston, said piston being retained by said second trigger means (19), said appendix of said slider (5) being formed by an upper extended part of said slider (5) with an upper edge, said second trigger means (19) being adapted to be released by said upper edge.

3. An auto-injector according to claim 2, wherein said second trigger means (19) comprises at least one detent tooth, projecting into said bore of said casing (14) for retaining said piston, means for urging said at least one tooth out of said bore, and said at least one tooth being maintained in said bore by means of a control sleeve (17) movable between two positions: one lower position in which said control sleeve (17) prevents said at least one tooth from getting out from said bore, and an upper position in which said at least one tooth is free to get out of said bore, said upper edge of said slider (5) being at a length such that, when said slider is about to completely uncover said needle, said upper edge engages said control sleeve (17) in the lower position and moves it upwards to the upper position.

4. An auto-injector according to claim 2, which further comprises a tubular protection cover (24) fixed to an upper end of casing (14),for covering said second device performing the injection.

5. An auto-injector according to claim 2, wherein said first trigger means (9) of said first device D1 comprise a detent slit ring (9) having one single slit, automatic safety needle protection means are provided, said protection means including an elastic sleeve (31) placed around said casing (14) and movable between a lower position and an upper position, a seat (35) formed on the upper part of said slider, for receiving said elastic sleeve in a deformed state in its lower position, a return spring (36) for moving back said slider in its initial position after completion of the injection when said auto-injector is moved away from the user's body, at least one part of said elastic sleeve being in pressure contact with one of said casing (14) and said protection cover (24) so that friction so provided is light enough not to prevent a snap rearward movement of said slider, but high enough to cause a friction force which is greater than a friction force against the seat (35), so that during said snap movement, said elastic sleeve is pushed upwards to the upper position and when the slider is pushed back by the return spring, the elastic sleeve remains in said upper position, the length of said elastic sleeve being slightly shorter than the stroke of the slider, whereby said elastic sleeve completely gets out from said seat (35) and returns to its free state, thus irreversibly locking said slider into a needle protection position.

6. An auto-injector according to claim 1, wherein said slider (5) is disposed outside and around said cylindrical body (1).

7. An auto-injector according to claim 2, wherein said connecting means comprise flexible teeth (13) on the lower end of said casing (14) and sloes (12) on the cylindrical carrying body (1).

8. An auto-injector according to claim 3, wherein said second trigger means comprise a resilient expansible slit ring (19) provided with detent teeth, operating in a circular groove (20) formed on said casing (14), provided with slots through which said dement teeth of the ring (19) inwardly protrude inside the bore of said casing.

9. An auto-injector according to claim 4, wherein said tubular protection cover (24) is provided with a flexible radial arm (25) carrying two safety pins (26, 27) intended to be inserted into two corresponding holes (28, 29) formed into said cover (24) in such a position that, when inserted, and with the auto-injector not actuated, the lower pin (27) rest against the edge of the slider (5) while the upper pin (26) rests against an annular shoulder (30) formed on the control sleeve (17), thereby preventing upper movement of the slider and the control sleeve and acting therefore as a safety device.

10. An auto-injector according to claim 5, wherein said elastic sleeve (31) is formed with a longitudinal slit (37), with an upper cylindrical portion (32) provided with an annular projection (33) adapted to slide with friction against the inside wall of cover (24), and with a lower thinner flexible portion which is provided with longitudinal slits.

11. An auto-injector for a medicament prefilled syringe (4, 404), having a head at one end and fitted with a needle (10, 410) at the other end and including a syringe piston (23), said auto-injector incorporating a first device D1 which makes automatic the needle penetration into a user's body by releasing of a first trigger means (9, 419) and controls a second device D2 which performs the medicament injection, said first device D1 comprising a slider (5, 405) concentric to said syringe (4, 404), and adapted to be connected to said syringe by means of said first trigger means (9, 419), in a position in which it covers said needle, said first trigger means (9, 419) being releasable when applying a predetermined force on said syringe (4, 404) when said slider (5, 405) is placed against the user's body, said second device D2 comprising a piston (21) resting against the syringe piston (23) urged by a compressed spring (22), and second trigger means (19) retaining said piston (21), characterized in that said slider (5, 405) is fitted with an appendix disposed for releasing said second trigger means (19) of said second device D2 when a reciprocal movement of said slider is completed with the result of having the medicament injection beginning only after the complete needle penetration thereby avoiding any medicament delivery at a non-desired depth or site.

12. An auto-injector according to claim 11 wherein at least one of said first and second trigger means comprises a resilient expansible slit ring (9, 419; 19).

* * * * *